United States Patent
Kim et al.

(10) Patent No.: US 6,928,323 B2
(45) Date of Patent: Aug. 9, 2005

(54) ADAPTIVE SENSING THRESHOLD FOR CROSS-CHAMBER REFRACTORY PERIOD

(75) Inventors: Jaeho Kim, Redmond, WA (US); Harley White, Carnation, WA (US); Anthony Harrington, Woodinville, WA (US); Joseph M. Bocek, Seattle, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 285 days.

(21) Appl. No.: 10/334,217

(22) Filed: Dec. 30, 2002

(65) Prior Publication Data

US 2004/0127947 A1 Jul. 1, 2004

(51) Int. Cl.[7] ............................................. A61N 1/37
(52) U.S. Cl. ............................................................ 607/9
(58) Field of Search ...................................... 607/9–31

(56) References Cited

U.S. PATENT DOCUMENTS

| | | | |
|---|---|---|---|
| 5,339,820 A | 8/1994 | Henry et al. | 128/696 |
| 5,620,466 A | 4/1997 | Haefner et al. | 607/5 |
| 5,658,317 A | 8/1997 | Haefner et al. | 607/5 |
| 5,662,688 A | 9/1997 | Haefner et al. | 607/5 |
| 5,690,683 A | 11/1997 | Haefner et al. | 607/4 |
| 5,709,215 A | 1/1998 | Perttu et al. | 128/708 |
| 5,755,738 A | 5/1998 | Kim et al. | 607/9 |
| 5,755,739 A | 5/1998 | Sun et al. | 607/14 |
| 5,991,657 A | 11/1999 | Kim | 607/5 |
| 6,169,918 B1 | 1/2001 | Haefner et al. | 600/509 |

FOREIGN PATENT DOCUMENTS

WO    WO-0024460 A1    5/2000

*Primary Examiner*—Scott M. Getzow
(74) *Attorney, Agent, or Firm*—Schwegman, Lundberg, Woessner & Kluth, P.A.

(57) ABSTRACT

A cross-chamber refractory period with an adaptively adjusted sensing threshold for use by a cardiac pacemaker is disclosed. In response to a cross-chamber event, the sensing threshold of a sensing channel is raised to an adaptively adjusted cross-chamber maximum refractory value. The cross-chamber maximum refractory value is derived from a peak amplitude measurement of the far-field signal resulting from the cross-chamber event.

36 Claims, 5 Drawing Sheets

ADAPTIVE SENSING THRESHOLD FOR CROSS-CHAMBER REFRACTORY PERIOD

FIELD OF THE INVENTION

This disclosure pertains to cardiac pacemakers and methods for their operation. In particular, the invention relates to sensing refractory periods and sensing thresholds.

BACKGROUND

Implantable cardiac pacemakers are a class of cardiac rhythm management devices that provide electrical stimulation in the form of pacing pulses to selected chambers of the heart. (As the term is used herein, a pacemaker is any cardiac rhythm management device with a pacing functionality regardless of any additional functions it may perform such as cardioversion/defibrillation.) Most pacemakers are used in the treatment of bradycardia by enforcing a minimum heart rate and/or restoring atrio-ventricular conduction in order to make up for a heart's inability to pace itself at an appropriate rhythm. Also included within the concept of cardiac rhythm is the manner and degree to which the heart chambers contract during a cardiac cycle to result in the efficient pumping of blood. Pacemakers have been developed which provide electrical pacing stimulation to one or both of the atria and/or ventricles at single or multiple sites during a cardiac cycle in an attempt to improve the coordination of atrial and/or ventricular contractions, termed cardiac resynchronization therapy. Such multiple paces are usually delivered to a heart chamber during a cardiac cycle with a pacing mode similar to that used for bradycardia pacing.

In pacemakers with sensing channels for sensing one or more heart chambers, the ventricular and/or atrial sensing channels are rendered refractory following certain events, such that certain sensed signals are ignored for the duration of the period. Sensing channels are rendered refractory in order to prevent the misinterpretation of electrogram signals resulting from a pace or a previous depolarization in the heart chamber sensed by the channel. A sensing channel may also be rendered refractory for a period of time in response to a pace or depolarization in a heart chamber different from the chamber sensed by the channel. Such refractory periods are called cross-chamber refractory periods.

SUMMARY OF THE INVENTION

In accordance with the present invention, a cross-chamber refractory period in a sensing channel for a first heart chamber which is initiated in response to a pace or sense in a second heart chamber is implemented by raising the sensing threshold of the channel above its steady-state value. The sensing threshold is raised during the cross-chamber post-event refractory period to a specified maximum value, referred to as the cross-chamber maximum refractory value, which is derived from the measured peak amplitude of the far-field signal received by the sensing channel when a pace or sense occurs in the second heart chamber. Separate post-pace and post-sense cross-chamber maximum refractory values may be derived from one or more previously measured peak amplitudes of the far-field electrogram signal. The maximum refractory values in each case are derived such that the sensing channel ignores the far-field signal from the pace or sense but still detects an actual chamber sense from an electrogram signal of higher amplitude than the far-field signal.

DETAILED DESCRIPTION

Figure 1:
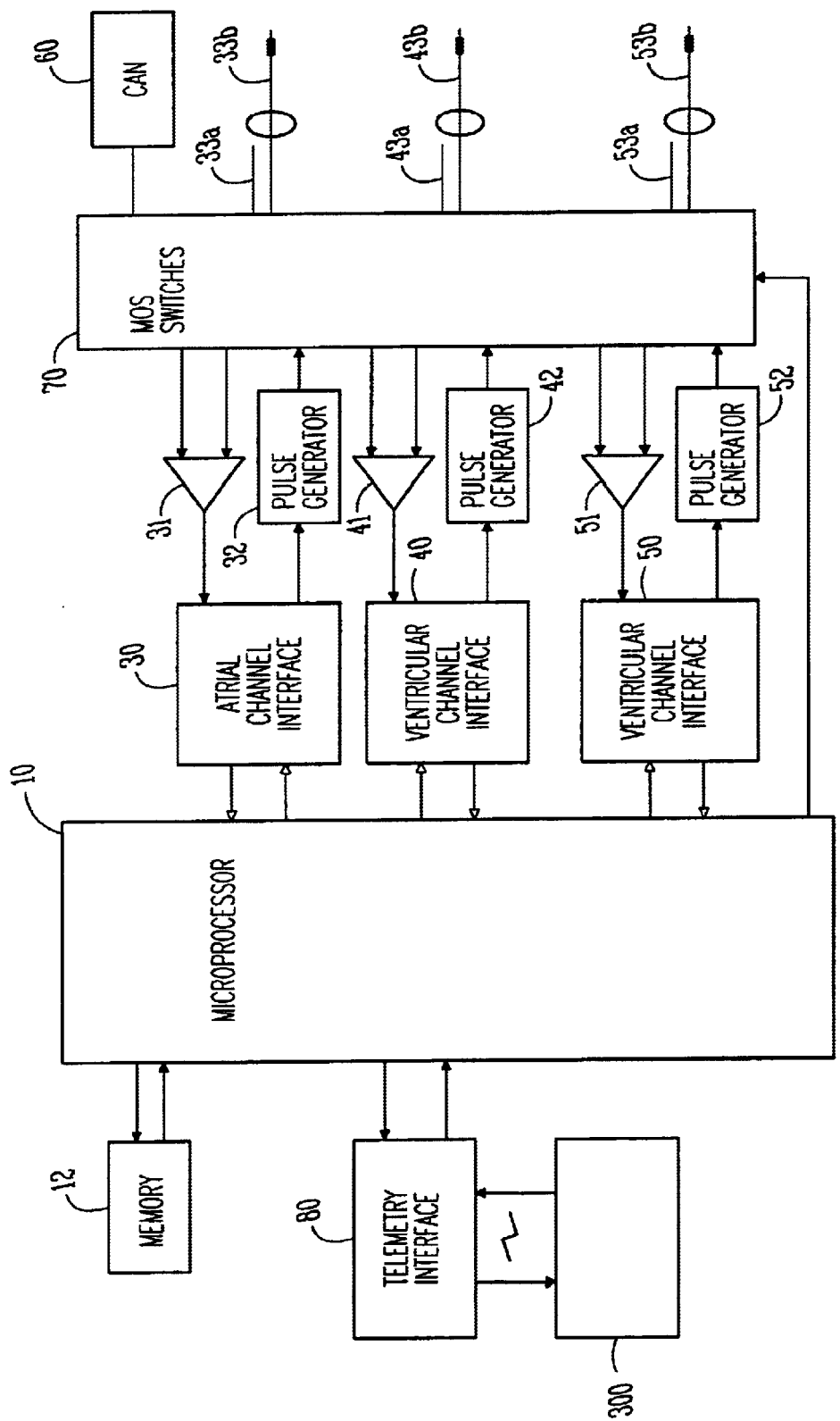
FIG. 1 is a block diagram of a multi-site pacemaker.

The present invention may be incorporated into pacemakers having a number of different pacing configurations, including multi-site pacing configurations for delivering various types of resynchronization therapy where a pace is delivered to each of the paired atria and/or ventricles during a cardiac cycle or where multiple paces are delivered to a single chamber. For illustrative purposes, however, the invention will be described with reference to a dual-chamber pacemaker (i.e., one that senses and/or paces both the atria and ventricles) having two ventricular pacing channels for pacing both ventricles or delivering two paces to a single ventricle as shown in FIG. 1.

a. Hardware Platform

Pacemakers are typically implanted subcutaneously on a patient's chest and have leads threaded intravenously into the heart to connect the device to electrodes used for sensing and pacing. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) is delivered to the chamber.

The controller of the pacemaker is made up of a microprocessor 10 communicating with a memory 12, where the memory 12 may comprise a ROM (read-only memory) for program storage and a RAM (random-access memory) for data storage. A microprocessor-type controller 10 controls the overall operation of the device in accordance with programmed instructions stored in memory. The controller could be implemented by other types of logic circuitry (e.g., discrete components or programmable logic arrays) using a state machine type of design, but a microprocessor-based system is preferable. As used herein, the term "circuitry" should be taken to refer to either discrete logic circuitry or to the programming of a microprocessor. A telemetry interface 80 is provided for communicating with an external programmer 300. The external programmer is a computerized device that can interrogate the pacemaker and receive stored data as well as adjust the operating parameters of the pacemaker.

The controller is capable of operating the pacemaker in a number of programmed modes where a programmed mode defines how pacing pulses are output in response to sensed events and expiration of time intervals. The controller causes the pacing pulses to be output in response to lapsed time intervals and sensed electrical activity (i.e., intrinsic heart beats) in accordance with a programmed mode. Most pacemakers are programmed to operate in an inhibited demand mode (a.k.a., synchronous mode), where a pacing pulse is delivered to a heart chamber during a cardiac cycle only when no intrinsic beat by the chamber is detected. An escape interval is defined for each paced chamber, which is the minimum time interval in which a beat must be detected before a pace will be delivered. The ventricular escape interval, for example, is reset by each ventricular sense or pace and thus defines the minimum rate at which the pacemaker will allow the ventricles to beat, sometimes referred to as the lower rate limit. A similar escape interval can be defined for pacing the atria. An escape interval can also be defined for pacing the ventricles in an atrial tracking or AV sequential mode, where the escape interval, referred to as the atrio-ventricular interval, is triggered by an atrial sense or pace and stopped by a ventricular sense.

The device is equipped with multiple sensing amplifiers and pulse generators which can be configured as channels for pacing and/or sensing selected heart chambers. A MOS switching network 70 controlled by the microprocessor is used to configure a sensing or pacing channel by switching selected electrodes to the input of a sense amplifier or to the output of a pulse generator. The switching network 70 also allows the device to employ either bipolar sensing/pacing using two closely spaced electrodes of a lead or unipolar sensing/pacing using one of the electrodes of a lead and the can 60 as a reference electrode. The device shown in FIG. 1 is configured with an atrial channel for sensing or pacing an atrial site which comprises a bipolar lead with a ring electrode 33*a* and a tip electrode 33*b*, sense amplifier 31, pulse generator 32, and an atrial channel interface 30 which communicates bidirectionally with a port of microprocessor 10. The device also has two ventricular channels for sensing or pacing ventricular sites which similarly include bipolar leads with ring electrodes 43*a* and 53*a* and tip electrodes 43*b* and 53*b*, sense amplifiers 41 and 51, pulse generators 42 and 52, and ventricular channel interfaces 40 and 50. The channel interfaces may include comparators for comparing received electrogram signals to reference values, analog-to-digital converters for digitizing sensing signal inputs from the sensing amplifiers, registers that can be written to for adjusting the gain and threshold values of the sensing amplifiers, and registers for controlling the output of pacing pulses and/or adjusting the pacing pulse energy by changing the pulse amplitude or pulse width.

The controller uses the sensing channels in order to detect intrinsic cardiac activity in a heart chamber, referred to as a chamber sense (e.g., an atrial sense or a ventricular sense). Such detected chamber senses are then used for controlling the delivery of paces in accordance with a programmed pacing mode and/or for diagnostic purposes. In an inhibited demand pacing mode, for example, chamber senses are used to inhibit pacing, while in a triggered pacing mode chamber senses are used to trigger pacing pulses. By counting the number of senses over a defined time period, the controller is also able to measure heart rate and detect arrhythmias using a rate-based criterion. As described above, a sensing channel includes sense amplifier circuits for amplifying and filtering the electrogram signals picked up by an electrode disposed at a cardiac site. In order to detect intrinsic cardiac activity, the signals emanating from the sense amplifier are compared with a reference potential. Only when an electrogram signal from the sense amplifier exceeds a reference potential threshold will it be treated as a chamber sense. The reference potential may thus be referred to as a sensing threshold. The sensing threshold may be implemented with analog circuitry, where the sense amplifier output is applied to one input of a comparator circuit whose other input is connected to a reference potential, or with digital circuitry operating on digitized samples of the sense amplifier output which are compared with a digitized reference value. In either case, the sensing threshold for each channel is adjustable by the controller. A clinician communicating with the controller may thus adjust the sensing threshold to give a desired degree of sensitivity and specificity so that noise from various sources is ignored while true depolarizations are detected as chamber senses. As described below, the controller may also be programmed to manipulate the sensing threshold of a sensing channel in order to implement sensing refractory periods.

b. Sensing Refractory Periods

A sensing refractory period for a sensing channel is a time period during which the channel is rendered relatively or absolutely insensitive to what would otherwise be interpreted as intrinsic cardiac activity for the purposes of diagnostic counting or for triggering or inhibiting paces. A sensing refractory period may be used, for example, to avoid interpreting the electrogram signal immediately following a detected intrinsic depolarization or pacing pulse as another chamber sense. In the former case, a sensing channel is rendered refractory for a post-sense refractory period once a sense is detected in that channel in order to prevent ongoing depolarization from being detected as a chamber sense. In the case of a pacing pulse, a sensing channel is rendered refractory for a post-pace refractory period after a pace is delivered though that channel in order to prevent both the pacing pulse and the depolarization evoked by the pace from being detected as a chamber sense.

Refractory periods may be implemented in at least two different ways. One way is to disable the sensing circuitry so that no electrogram signal is received. A post-pace refractory period, for example, may be at least partly implemented with a so-called blanking interval in which a sensing amplifier of the sensing/pacing channel is blanked (i.e., disabled) immediately upon delivery of a pacing pulse. One way of implementing blanking is to disconnect the sense amplifier from the sensing electrodes via the MOS switching network 70. Blanking the sensing amplifier both prevents the pacing pulse from re-entering the amplifier's input where it would cause saturation of the amplifier and avoids amplifying the large amplitude after-potentials generated by polarization of the electrodes after the pace. A blanking interval is an example of an absolute refractory period during which no chamber sense will be detected regardless of the magnitude of the electrogram signal. Another way to render a sensing channel refractory is to raise the sensing threshold above its normal or steady-state value. Raising the sensing threshold may either implement an absolute refractory period (i.e., by increasing the threshold to infinity or some maximum allowable value) or a relative refractory period where a larger magnitude electrogram signal is required for detection of a chamber sense than is the case during normal operation. Implementing a refractory period by raising the sensing threshold may be referred to as soft-blanking as opposed to normal blanking where the sensing amplifier is disabled. With soft-blanking, although the sensing channel is rendered absolutely or relatively insensitive with respect to chamber sense detection, the electrogram signal is still received by the sensing circuitry and may be measured or used for other purposes.

As aforesaid, one of the reasons for initiating a refractory period in a sensing channel is to prevent the detection of a chamber sense shortly after detection of a sense or delivery of a pace. If the channel were not made refractory, the electrogram signal due to areas of the myocardium continuing to depolarize could be interpreted as another chamber sense when it is actually part of the same contraction. An electrogram signal that would be wrongly interpreted as a chamber sense by a sensing channel under normal sensing conditions is referred to herein as an artifact. Interpreting an artifact as a chamber sense, or oversensing, can result in, among other things, inappropriate pacing rates, undesirable inhibition of pacing pulses, and/or misdiagnoses of arrhythmias. This problem can be avoided after a sense or pace by blinding the sensing channel to chamber senses during a period of time when it is considered highly improbable that another contraction of the sensed chamber would occur. A post-sense absolute refractory period would thus begin immediately after detection of sense, while a post-pace absolute refractory period would begin upon delivery of a pace after the end of any blanking interval.

Completely blinding a sensing channel with an absolute refractory period, however, presents a risk of undersensing. Undersensing occurs when the channel fails to detect a chamber sense when an actual contraction occurs and can result in inappropriate pacing rates, failure to detect arrhythmias, and/or asynchronous pacing. In order to lessen the risk of undersensing, a relative refractory period can be utilized instead of an absolute refractory period. In a soft-blanked relative refractory period, the sensing threshold is raised above the normal steady-state value in order to not detect an artifact, but an electrogram signal of sufficient amplitude will still be detected as a chamber sense. The two approaches can be combined by initiating a post-pace or post-sense absolute refractory period after the pace or sense which is immediately followed by a relative refractory period. The total post-sense or post-pace refractory period is then made up of an absolute refractory period (including any initial blanking interval in the case of a pace) during which no chamber senses are permitted and a relative refractory period during which the sensing threshold is raised to a supranormal value. (The refractory period can also include other intervals such as a retriggerable noise interval.) When the refractory period starts, the sensing threshold is raised to a specified value selected to be above the channel's steady-state value. After a specified time period, the sensing threshold is then abruptly returned to the steady-state value or may decay to the steady-state value in a gradual (continuous or step-wise) fashion. The refractory sensing threshold value to which the sensing threshold is raised during a post-pace or post-sense relative refractory period can either be a programmable fixed value or may be adaptively determined by the implantable device. One scheme for adaptively adjusting the refractory sensing threshold value involves measurement of the peak amplitude of the electrogram signal during the soft-blanked absolute refractory period immediately following a chamber sense or a pace and then setting the maximum refractory sensing threshold value to a specified fraction (e.g., 75%) of the measured peak amplitude (or of an average of previously measured peak amplitudes).

As described above, a post-pace or post-pace refractory period can be implemented in the same channel in which a pace or sense occurs, referred to as a same-chamber refractory period, in order to prevent interpreting any continuing depolarization as another chamber sense. Another problem that arises when sensing depolarizations at a particular local cardiac site with a sensing channel dedicated to that site, however, is the additional sensing of electrogram signals that originate from another cardiac site or a pace delivered to that site, referred to as a far-field signal. When sensing channels are provided for multiple chambers (e.g., an atrium and a ventricle, both atria, and/or both ventricles), sensing by a sensing channel dedicated to one chamber of far-field signals produced by another chamber or a pace to that chamber can produce a form of cross-talk between the sensing channels. Cross-talk between sensing channels occurs when a sensing channel senses a far-field artifact and interprets it as a chamber sense. In order to prevent cross-talk between channels, a cross-chamber refractory period can be implemented in a channel so that it is rendered less sensitive upon detection of a depolarization in another chamber or when a pace is delivered to that chamber, referred to as a cross-chamber refractory period. A well-known example of a cross-chamber refractory period is the post-ventricular atrial refractory period, or PVARP, used to prevent an atrial sensing channel from interpreting ventricular depolarizations as atrial senses which causes a pacemaker-mediated tachycardia in an atrial-tracking pacing mode.

Soft-blanking, as described above with respect to same-chamber refractory periods, can be used to implement both post-pace cross-chamber and post-sense refractory periods. (See U.S. Pat. No. 6,169,918 assigned to Cardiac Pacemakers, Inc. and hereby incorporated by reference in its entirety.) One way of implementing a post-sense cross-chamber or post-pace refractory period is to raise the sensing threshold of a first chamber sensing channel above its steady-state value upon detection of a depolarization in a second chamber sensing channel or upon delivery of a pace to the second chamber, where the sensing threshold is raised to a value during the cross-chamber refractory period which is equal to the channel's same-chamber refractory sensing threshold value or some specified fraction thereof. As the same-chamber refractory sensing threshold value of the channel adapts based upon the measured peak amplitude of electrogram signals following chamber senses or paces, therefore, so too does the cross-chamber refractory sensing threshold value. This technique may not result in an optimum level of sensitivity and specificity for the channel during the cross-chamber refractory period, however, because the cross-chamber refractory sensing threshold value is determined without regard to the amplitude of the actual far-field signals received by it.

c. Adaptive Sensing Threshold for Cross-Chamber Soft-Blanking

Rather than adjusting a sensing channel's cross-chamber refractory sensing threshold based upon measured peak electrogram amplitudes during same-chamber senses and paces, the present invention proposes that the cross-chamber refractory sensing threshold be adaptively adjusted in accordance with measured peak amplitudes of the far-field electrogram signal received during cross-chamber senses and/or paces. In this way, the performance of the sensing channel during the cross-chamber refractory period in rejecting far-field artifacts as chamber senses while continuing to detect actual chamber senses can be made more nearly optimum.

A post-sense cross-chamber or post-pace refractory period may be implemented generally by setting the sensing threshold of a channel equal to a time-varying function that exceeds the channel's steady-state value over the course of the refractory period. In one implementation, for example, sensing threshold is abruptly raised to a specified refractory value at the start of the refractory period and abruptly lowered to the steady-state value at the end of the refractory period. The sensing threshold may alternatively be made to decay toward the steady-state value during the refractory period in some specified manner. In another implementation, rather than being abruptly raised to a specified refractory value, the sensing threshold is a time-varying function that rises to a specified maximum refractory value at a specified time during the refractory period and then falls toward the steady-state value in a specified manner during the remainder of the period. In the case where a time-varying sensing threshold rises to its maximum refractory value after a delay interval and/or falls from its maximum refractory value before the end of the refractory period, the sensing threshold should be maintained at its maximum refractory value during a time period in which the far-field signal is expected to occur. To accomplish this, the time at which a far-field signal occurs relative to a preceding pace or sense in another channel can be measured in an individual patient after implantation and then used to define the time-varying cross-chamber sensing threshold function.

Whether implemented as a constant function or a time-varying function, the cross-chamber refractory sensing threshold can be characterized by a maximum refractory value which represents the maximum value of the sensing threshold during the cross-chamber refractory period. The maximum refractory value for each cross-chamber refractory period may then be derived as either a linear or non-linear function of the measured peak amplitudes of one or more far-field electrogram signals received during cross-chamber senses and/or paces. Thus, a post-pace cross-chamber refractory period for a first chamber sensing channel is implemented by raising the channel's sensing threshold above its steady-state value upon delivery of a pace to a second chamber, where the maximum value of the sensing threshold during the period is a post-pace cross-chamber maximum refractory value derived from one or more previous peak amplitude measurements of the electrogram signal received by the first chamber sensing channel during a second chamber pace. In order to derive the post-pace cross-chamber maximum refractory value, the device goes through a training period consisting of specified number of cardiac cycles in which the second chamber is paced and the peak amplitude of the resulting far-field electrogram signal in the first chamber sensing channel is measured. After completion of the training period, a post-pace cross-chamber maximum refractory value is derived from the measured peak amplitudes by, for example, multiplying the measured peak amplitude by a specified fraction greater than one. The derived post-pace cross-chamber maximum refractory value can then be used in implementing the refractory period in the first chamber sensing channel after subsequent second chamber paces. Similarly, a post-sense cross-chamber refractory period is implemented by raising the sensing threshold of the first chamber sensing channel above its steady-state value upon detection of a second chamber sense, where the maximum value of the sensing threshold during the period is a post-sense cross-chamber maximum refractory value derived from one or more previous peak amplitude measurements of the electrogram signal received by the first chamber sensing channel after a second chamber sense. A similar training period may be used to derive the post-sense cross-chamber maximum refractory value for use by the first chamber sensing channel when a second chamber sense is detected. During the training period, the peak amplitude of the resulting far-field electrogram signal in the first chamber sensing channel is measured upon detection of a second chamber sense. A specified number of such peak amplitude measurements are then used to derive a post-sense cross-chamber refractory sensing threshold value (again, e.g., by multiplying the peak amplitude measurement by a specified fraction greater than one).

During the training periods, a specified number of peak amplitude measurements of the far-field electrogram during post-sense and post-pace periods are recorded, where the specified number of measurements is one or greater. In an embodiment where multiple peak amplitude measurements are recorded, the peak amplitude measurement used to derive a post-sense or post-pace maximum refractory value may then constitute a statistical function of the multiple peak amplitude measurements recorded during the training period. Such a statistical function may be, for example, a median value, an average, or a weighted average with specified weighting coefficients. In another embodiment, post-sense and post-pace cross-chamber maximum refractory values may be derived after each cross-chamber sense and pace, respectively, and then moving averaged with one or more previously derived post-sense or post-pace maximum refractory values. Before the maximum refractory values are derived in either embodiment, the device may be programmed to use an alternative maximum refractory value for the post-pace and post-sense cross-chamber refractory periods. For example, when a post-pace maximum refractory value has been derived but not a post-sense maximum refractory value, the former may be used in place of the latter and vice-versa. An alternative maximum refractory value may also be a programmable fixed value or a value derived from a sensing threshold value used for same-chamber refractory periods.

The cross-chamber refractory periods described above operate in conjunction with same-chamber refractory periods so that a cross-chamber refractory sensing threshold value at the time of a cross-chamber event may be less than the current sensing threshold of the sensing channel due to, for example, the continuation of a previous same-chamber refractory period. The device may be programmed to deal with this situation by selecting the higher sensing threshold. That is, the circuitry for rendering a sensing channel refractory for a post-sense or post-sense cross-chamber refractory period raises the channel sensing threshold to a value dictated by either the cross-chamber refractory period or the same-chamber refractory period, whichever is greater, when the cross-chamber refractory period and the same-chamber refractory period overlap.

Figure 2A:
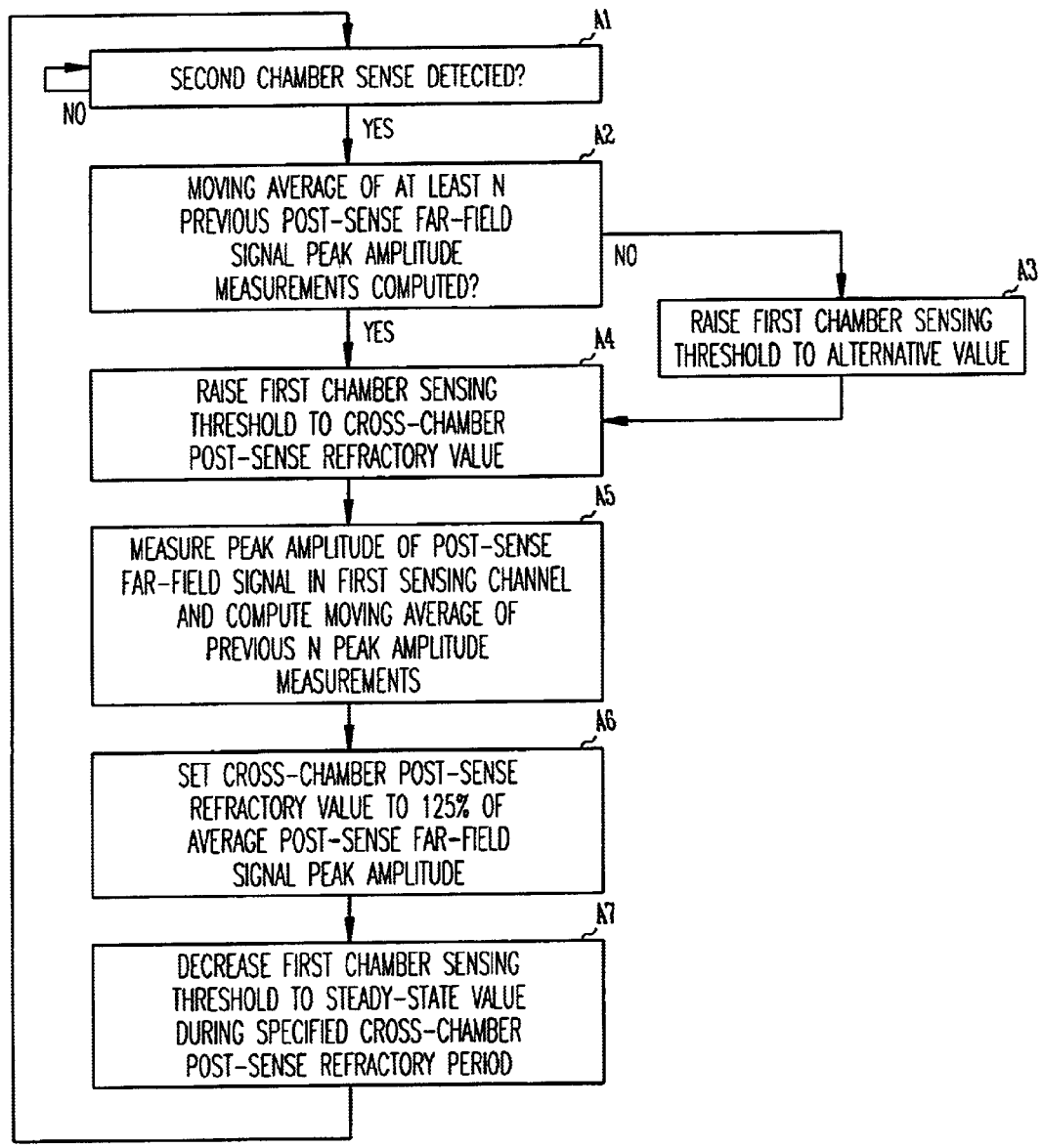
FIGS. 2A and 2B illustrate the steps of an exemplary routine for implementing a cross-chamber refractory period with an adaptively adjusted sensing threshold.
Figure 2B:
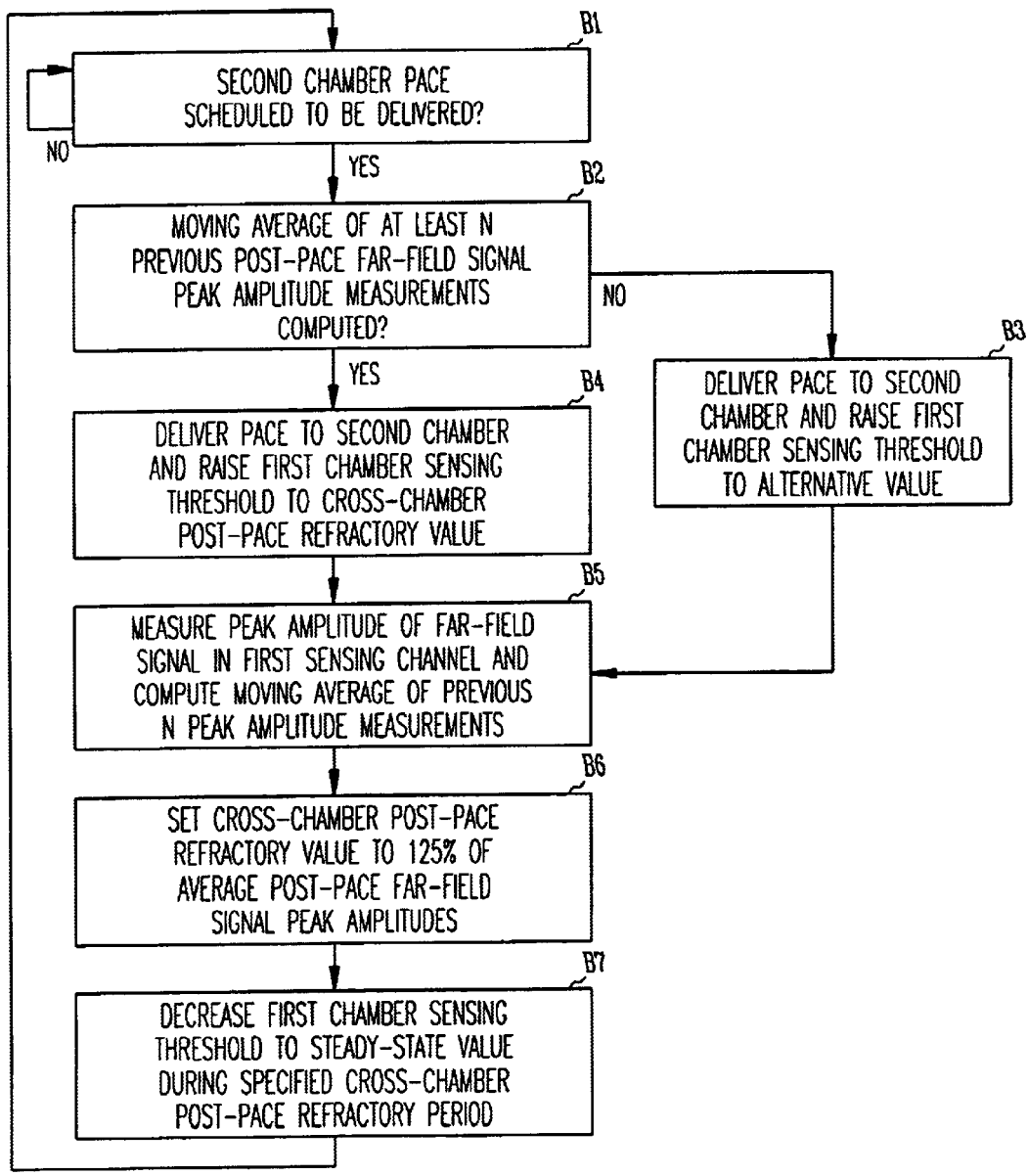

In an exemplary implementation, the sensing channels of a cardiac rhythm management device such as illustrated in FIG. 1 are configured to sense first and second chambers of the heart, where the first and second chambers may be an atrium and a ventricle, a ventricle and an atrium, the paired atria, or the paired ventricles. The controller may be programmed to implement same-chamber post-pace and post-sense refractory periods for each channel in the manner described above so that the refractory sensing thresholds are adaptively adjusted based upon a measured peak amplitude of the received electrogram signal after a pace or sense. FIGS. 2A and 2B illustrate a specific procedure for implementing cross-chamber refractory periods in the first chamber sensing channel upon detection of a second chamber sense or delivery of a second chamber pace. The device utilizes adaptively adjusted sensing thresholds for the cross-chamber refractory periods based upon measurements of the peak amplitudes of post-sense and post-pace far-field electrogram signal in the first chamber sensing channel.

Referring to FIG. 2A, after a second chamber sense is detected at step A1, the device tests at step A2 whether a moving average of at least N previous post-sense far-field signal peak amplitude measurements have been computed, where N is an integer greater than or equal to 1. If so, the device starts a post-sense cross-chamber refractory period in the first channel sensing channel by raising the sensing threshold above its steady-state value and to a previously derived post-sense cross-chamber maximum refractory value at step A4. If N far-field peak amplitude measurements have not yet been taken, the sensing threshold is raised to an alternative maximum value at step A3. At step A5, the peak amplitude of the post-sense far-field signal in the first sensing channel is measured, and a moving average of the previous N peak amplitude measurements is computed. The post-sense cross-chamber maximum refractory value is then derived at step A6 by multiplying the average post-sense far-field signal peak amplitude by a proportionality factor, in this case 125%. At step A7, the first chamber sensing threshold is decreased, either abruptly or gradually, to the steady-state value over the course of the post-sense cross-chamber refractory period, and the routine returns to step A1.

FIG. 2B shows a similar routine for implementing a post-pace cross-chamber refractory period in the first channel. When a second chamber pace is scheduled to be delivered, as determined at step B1, the device checks if N peak amplitude measurements of the post-pace far-field signal have been taken at step B2. If so, the device delivers the second chamber pace and raises the first chamber sensing threshold above its steady-state value and to the derived post-pace cross-chamber maximum refractory value at step B4. Otherwise, the device delivers the second chamber pace and raises the first chamber sensing threshold to an alternative maximum value at step B3. Steps B5 through B7 are similar to steps A5 through A7 of FIG. 2A.

Figure 3A:
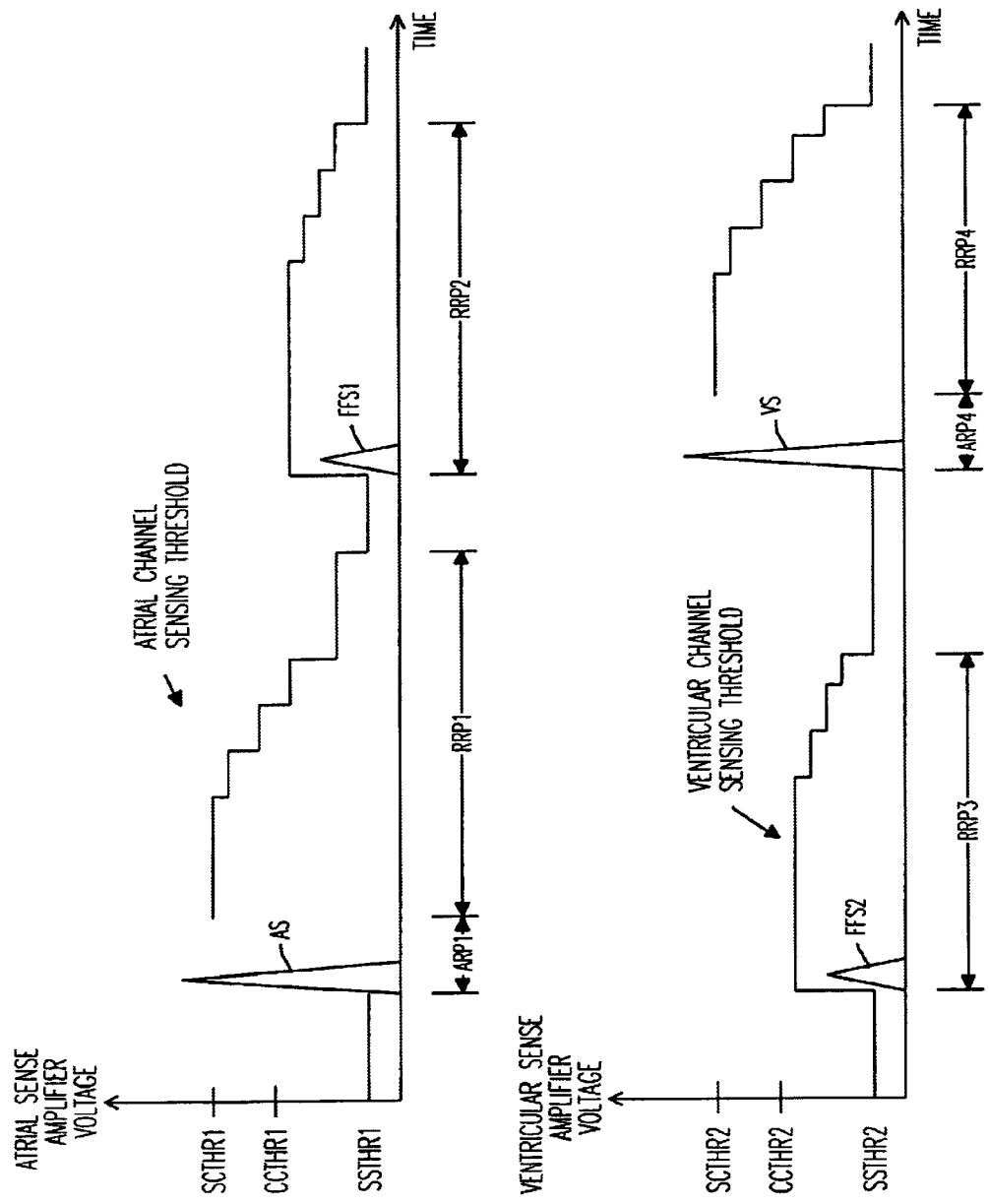
FIGS. 3A and 3B are diagrams illustrating the operation of cross-chamber refractory periods with adaptively adjusted sensing thresholds.
Figure 3B:
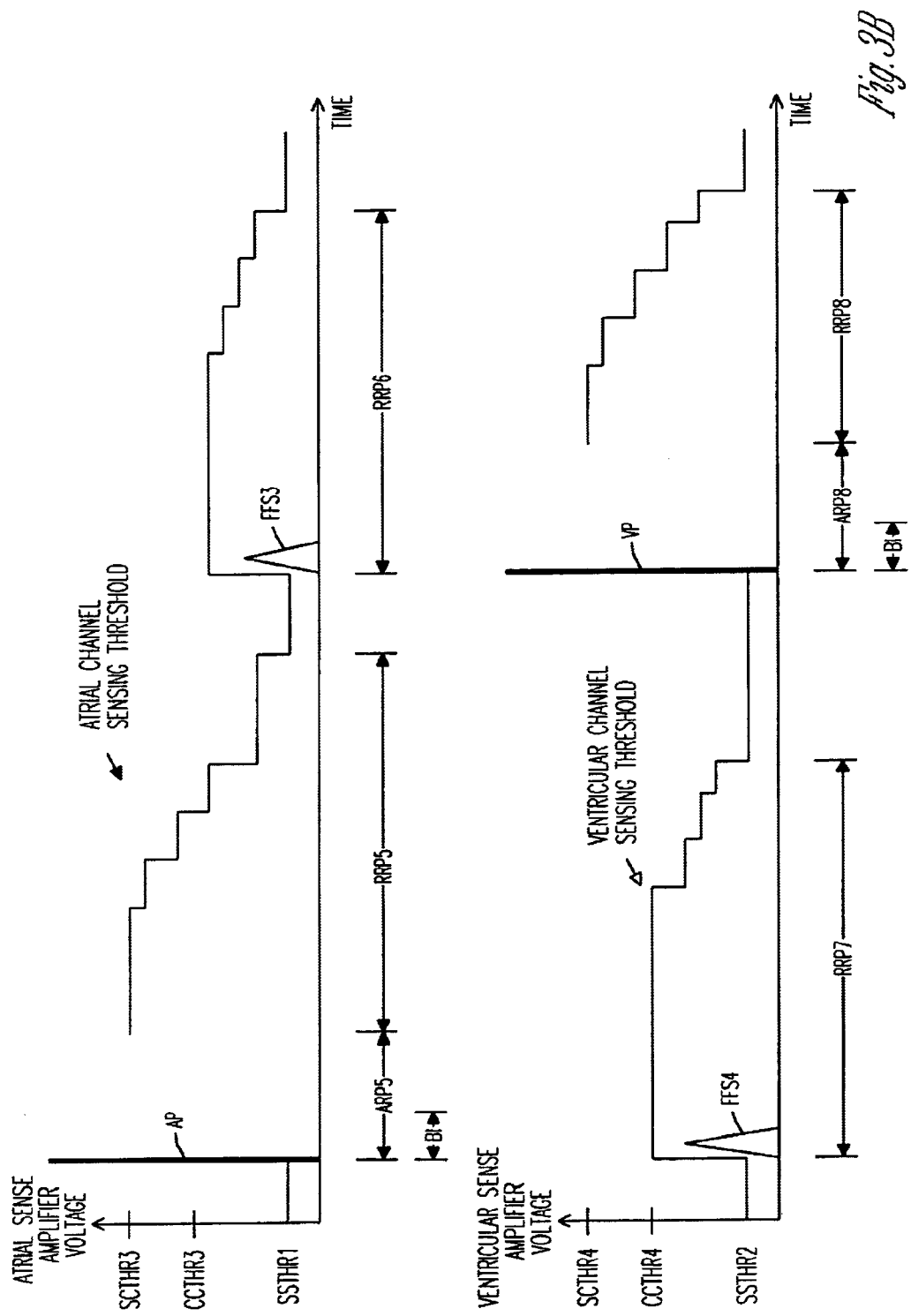

FIGS. 3A and 3B illustrate the operation of exemplary same-chamber and cross-chamber refractory periods as implemented in atrial and ventricular sensing channels. Both figures show simultaneous sensing events in atrial and ventricular channels where the sensing amplifier voltage is plotted against time in both channels. FIG. 3A illustrates the operation of post-sense refractory periods, while FIG. 3B illustrates post-pace refractory periods.

Referring first to FIG. 3A, an atrial sense AS is detected in the atrial channel which initiates an absolute refractory period ARP1 in that channel during which no further senses are permitted. Following the period ARP1, a relative refractory period RRP1 is started during which the atrial channel sensing threshold is raised from a steady-state value SSTHR1 to a same-chamber refractory threshold value SCTHR1, which has been derived from previous atrial senses to be a specified fraction (e.g., 75%) of the peak amplitude of the electrogram signal received by the channel during an atrial sense. Thus, the channel would detect another atrial sense if an electrogram signal of similar magnitude were to occur but would not detect electrogram signals smaller than SCTHR1 as senses. At the same time as the atrial sense occurs in the atrial channel, a cross-chamber relative refractory period RRP3 is started by raising the sensing threshold of the ventricular channel from a steady-state value SSTHR2 to a cross-chamber maximum refractory value CCTHR2 as the channel receives a far-field signal FFS2. The value CCTHR2 has been derived from one or more measurements of the peak amplitude of previous far-field signals during atrial senses to be a specified fraction greater than one (e.g., 125%) of the far-field signal amplitude. Thus, the far-field signal FFS2 is not interpreted as a ventricular sense, but the channel would continue to detect electrogram signals greater than CCTHR2 as ventricular senses. The sensing thresholds of both the atrial and ventricular channels are decreased toward their steady-state values during the refractory periods RRP1 and RRP3, respectively, to restore normal operation. A ventricular sense VS subsequently occurs in the ventricular sensing channel which causes the initiation of an absolute refractory period ARP4 after which the sensing threshold is raised from the steady-state value SSTHR2 to a same-chamber refractory value SCTHR2 to start relative refractory period RRP4. At the time of the ventricular sense VS, the sensing threshold of the atrial channel is raised from its steady-state value SSTHR1 to a cross-chamber maximum refractory value CCTHR1 as the channel receives a far-field signal FFS1. The value CCTHR1 has been derived from one or more measurements of the peak amplitude of previous far-field signals during ventricular senses to be a specified fraction greater than one (e.g., 125%) of the far-field signal amplitude. Thus, the far-field signal FFS1 is not interpreted as an atrial sense, but the channel would continue to detect electrogram signals greater than CCTHR1 as atrial senses. The sensing thresholds of both the atrial and ventricular channels are decreased toward their steady-state values during the refractory periods RRP2 and RRP4, respectively, to restore normal operation.

Referring next to FIG. 3B, an atrial pace AP is delivered in the atrial channel which starts an absolute refractory period ARP5 in that channel during which no further senses are permitted. The absolute refractory period includes an initial blanking interval BI, during which time the sensing amplifiers are disabled. Following the period ARP5, a relative refractory period RRP5 is started during which the atrial channel sensing threshold is raised from a steady-state value SSTHR1 to a same-chamber post-pace refractory threshold value SCTHR3, which has been derived during previous atrial paces to be a specified fraction (e.g., 75%) of the peak amplitude of the electrogram signal received by the channel after an atrial pace when the sensing amplifiers are enabled. Thus, the channel would detect an atrial sense if an electrogram signal greater than SCTHR3 were to occur. At the same time as the atrial pace is delivered, a post-pace cross-chamber relative refractory period RRP7 is started in the ventricular channel by raising the sensing threshold of the ventricular channel from a steady-state value SSTHR2 to a cross-chamber maximum refractory value CCTHR4 as the channel receives a far-field signal FFS4 resulting from the atrial pace. The value CCTHR4 has been derived from one or more measurements of the peak amplitude of previous far-field signals during atrial paces to be a specified fraction greater than one (e.g., 125%) of the far-field signal amplitude. Thus, the far-field signal FFS4 is not interpreted as a ventricular sense, but the channel would continue to detect electrogram signals greater than CCTHR4 as ventricular senses. The sensing thresholds of both the atrial and ventricular channels are decreased toward their steady-state values during the refractory periods RRP5 and RRP5, respectively, to restore normal operation. A ventricular pace VP subsequently occurs in the ventricular channel which causes the initiation of an absolute refractory period ARP8 which includes an initial blanking interval BI. The sensing threshold is then raised from the steady-state value SSTHR2 to a same-chamber refractory value SCTHR4 to start the same-chamber post-pace relative refractory period RRP8. At the time of the ventricular pace VP, the sensing threshold of the atrial channel is raised from its steady-state value SSTHR1 to a post-pace cross-chamber maximum refractory value CCTHR3 as the channel receives a far-field signal FFS3 resulting from the ventricular pace. The value CCTHR3 has been derived from one or more measurements of the peak amplitude of previous far-field signals during ventricular paces to be a specified fraction greater than one (e.g., 125%) of the far-field signal amplitude. Thus, the far-field signal FFS3 is not interpreted as an atrial sense, but the channel would continue to detect electrogram signals greater than CCTHR3 as atrial senses. The sensing thresholds of both the atrial and ventricular channels are decreased toward their steady-state values during the refractory periods RRP6 and RRP8, respectively, to restore normal operation.

In the embodiments described above, the peak amplitudes of far-field electrogram signals during cross-chamber paces and senses were measured and used to derive post-pace and post-sense maximum refractory values. In the case where the sensing amplifiers of the sensing channel have a time-varying gain (e.g., an automatic gain control), the peak amplitude measurements should be normalized with respect to the amplifier gain before being used to derive the maximum refractory values. Also, it is desirable for the peak amplitude measurements of far-field ventricular electrograms to only be taken during normal sinus rhythm. One way to detect a slow normal rhythm is to compare the time interval from a ventricular pace or sense to the following atrial sense to the threshold interval used for tachyarrhythmia detection. For example if tachyarrhythmia threshold rate is set to 170 bpm so that the tachyarrhythmia threshold interval is its reciprocal or 353 ms, then the time interval from a ventricular pace or sense to the following atrial sense should be longer than 353 ms before a valid peak amplitude measurement should be taken. A further constraint may be added so that the time interval from the end of any absolute refractory period after a ventricular sense or pace to a subsequent atrial sense should be longer than the tachyarrhythmia threshold interval. Alternatively, a normal rhythm for purposes of peak amplitude measurements may be defined as simply a ventricular rate which is less than a half of the tachyarrhythmia threshold rate.

The peak amplitude measurements may be used to derive other features of a post-pace or post-sense cross-chamber refractory sensing threshold function besides the maximum refractory value. For example, the peak amplitude of post-sense or post-pace far-field electrogram signal may also be used to derive an initial refractory sensing threshold value, a rate at which the refractory sensing threshold rises from an initial value to the maximum refractory value, a time from the start of the cross-chamber refractory period until the sensing threshold begins to decay toward the steady-state value, and the rate at which the sensing threshold decays toward the steady-state value.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A cardiac rhythm management device, comprising:
   first and second sensing channels for sensing electrical activity in a first heart chamber and a second heart chamber, respectively;
   circuitry for detecting a first chamber sense when the sensed electrical activity in the first sensing channel exceeds a first channel sensing threshold which has a minimum level equal to a specified first channel steady-state value;
   circuitry for detecting a second chamber sense when the sensed electrical activity in the second sensing channel exceeds a second channel sensing threshold which has a minimum level equal to a specified second channel steady-state value;
   circuitry for measuring a peak amplitude of a post-sense far-field signal generated in the first sensing channel after a second chamber sense is detected; and,
   circuitry for rendering the first sensing channel refractory for a post-sense cross-chamber refractory period after detection of a second chamber sense by raising the first channel sensing threshold above the first channel steady-state value, wherein the first channel sensing threshold is raised during the post-sense cross-chamber refractory period to a post-sense cross-chamber maximum refractory value derived from the measured peak amplitude of the post-sense far-field signal.

2. The device of claim 1 wherein the circuitry for rendering the first sensing channel refractory for a post-sense cross-chamber refractory period raises the first channel sensing threshold abruptly to the post-sense cross-chamber maximum refractory value after detection of a second chamber sense and subsequently decreases the first channel sensing threshold from the post-sense cross-chamber maximum refractory value toward the first steady-state value during the post-sense cross-chamber refractory period.

3. The device of claim 1 wherein the circuitry for rendering the first sensing channel refractory for a post-sense cross-chamber refractory period sets the first channel sensing threshold equal to a time-varying function after detection of a second chamber sense which rises to the post-sense cross-chamber maximum refractory value and subsequently decreases toward the first steady-state value during the post-sense cross-chamber refractory period.

4. The device of claim 3 wherein the time-varying function first rises to an initial post-sense cross-chamber refractory value derived from the measured peak amplitude of the post-sense far-field signal and subsequently increases to the post-sense cross-chamber maximum refractory value.

5. The device of claim 3 wherein the circuitry for rendering the first sensing channel refractory for a post-sense cross-chamber refractory period sets the first channel sensing threshold equal to first time-varying function after detection of a second chamber sense during a first cardiac cycle and sets the first channel sensing threshold equal to second time-varying function after detection of a second chamber sense during a subsequent cardiac cycle.

6. The device of claim 1 wherein the circuitry for rendering the first sensing channel refractory for a post-sense cross-chamber refractory period decreases the first channel sensing threshold from the post-sense cross-chamber maximum refractory value to the first channel steady-state value at the end of the post-sense cross-chamber refractory period.

7. The device of claim 1 wherein the circuitry for rendering the first sensing channel refractory for a post-sense cross-chamber refractory period decreases the first channel sensing threshold from the post-sense cross-chamber maximum refractory value to the first channel steady-state value at a decay rate derived from the measured peak amplitude of the post-sense far-field signal.

8. The device of claim 1 wherein the circuitry for rendering the first sensing channel refractory for a post-sense cross-chamber refractory period starts to decrease the first channel sensing threshold from the post-sense cross-chamber maximum refractory value toward the first channel steady-state value after a delay interval derived from the measured peak amplitude of the post-sense far-field signal.

9. The device of claim 1 wherein the circuitry for measuring the peak amplitude of the post-sense far-field signal measures the peak amplitude by computing a statistical function of the measured peak amplitudes of the post-sense far-field signal generated in the first sensing channel after a second chamber sense during a specified number of cardiac cycles.

10. The device of claim 1 wherein the post-sense cross-chamber maximum refractory value is approximately 125% of the measured peak amplitude of the post-sense far-field signal.

11. The device of claim 1 further comprising:
circuitry for rendering the first sensing channel refractory for a same-chamber refractory period upon detection of a first chamber sense or delivery of a first chamber pace by raising the first channel sensing threshold above the first channel steady-state value during the same-chamber refractory period; and,
wherein the circuitry for rendering the first sensing channel refractory for a post-sense cross-chamber refractory period raises the first channel sensing threshold to a value dictated by either the post-sense cross-chamber refractory period or the same-chamber refractory period, whichever is greater, when the post-sense cross-chamber refractory period and the same-chamber refractory period overlap.

12. The device of claim 1 further comprising:
circuitry for delivering paces to the second chamber;
circuitry for measuring a peak amplitude of a post-pace far-field signal generated in the first sensing channel when a second chamber pace is delivered; and
circuitry for rendering the first sensing channel refractory for a post-pace cross-chamber refractory period upon delivery of a second chamber pace by raising the first channel sensing threshold to a post-pace cross-chamber refractory value which is proportional to the measured post-pace far-field signal peak amplitude; and,
circuitry for rendering the first sensing channel refractory for a post-pace cross-chamber refractory period after delivery of a second chamber pace by raising the first channel sensing threshold above the first channel steady-state value, wherein the first channel sensing threshold is raised during the post-pace cross-chamber refractory period to a post-pace cross-chamber maximum refractory value derived from the measured peak amplitude of the post-pace far-field signal.

13. The device of claim 12 wherein the circuitry for rendering the first sensing channel refractory for post-sense cross-chamber and post-pace refractory periods raises the first sensing channel sensing threshold to an alternative maximum value during those periods if peak amplitudes of post-sense and post-pace far-field signals have not yet been measured.

14. The device of claim 1 wherein the circuitry for measuring a peak amplitude of a post-sense far-field signal generated in the first sensing channel after a second chamber sense is detected is configured to measure the peak amplitude only when a normal sinus rhythm is detected.

15. The device of claim 1 wherein the circuitry for measuring a peak amplitude of a post-sense far-field signal generated in the first sensing channel after a second chamber sense is detected is configured to measure the peak amplitude by computing a statistical function of the measured peak amplitudes of the post-sense far-field signal during a training period consisting of a specified number of cardiac cycles, and further wherein the circuitry for rendering the first sensing channel refractory does not derive the post-sense cross-chamber maximum refractory value from the measured peak amplitude until after completion of the training period.

16. A cardiac rhythm management device, comprising:
first and second sensing channels for sensing electrical activity in a first heart chamber and a second heart chamber, respectively;
circuitry for detecting a first chamber sense when the sensed electrical activity in the first sensing channel exceeds a -first channel sensing threshold which has a minimum level equal to a specified first channel steady-state value;
circuitry for detecting a second chamber sense when the sensed electrical activity in the second sensing channel exceeds a second channel sensing threshold which has a minimum level equal to a specified second channel steady-state value;
circuitry for delivering paces to the second chamber;
circuitry for measuring the peak amplitude of a post-pace far-field signal generated in the first sensing channel upon delivery of a second chamber pace; and
circuitry for rendering the first sensing channel refractory for a post-pace cross-chamber refractory period after delivery of a second chamber pace by raising the first channel sensing threshold above the first channel steady-state value, wherein the first channel sensing threshold is raised during the post-pace cross-chamber refractory period to a post-pace cross-chamber maximum refractory value derived from the measured peak amplitude of the post-pace far-field signal.

17. The device of claim 16 wherein the circuitry for rendering the first sensing channel refractory for a post-pace cross-chamber refractory period raises the first channel sensing threshold abruptly to the post-pace cross-chamber maximum refractory value after delivery of a second chamber pace and subsequently decreases the first channel sensing threshold from the post-pace cross-chamber maximum refractory value toward the first steady-state value during the post-pace cross-chamber refractory period.

18. The device of claim 16 wherein the circuitry for rendering the first sensing channel refractory for a post-pace cross-chamber refractory period sets the first channel sensing threshold equal to a time-varying function after delivery of a second chamber pace which rises to the post-pace cross-chamber maximum refractory value and subsequently decreases toward the first steady-state value during the post-pace cross-chamber refractory period.

19. The device of claim 18 wherein the time-varying function first rises to an initial post-pace cross-chamber refractory value derived from the measured peak amplitude of the post-pace far-field signal and subsequently increases to the post-pace cross-chamber maximum refractory value.

20. The device of claim 18 wherein the circuitry for rendering the first sensing channel refractory for a post-pace cross-chamber refractory period sets the first channel sensing threshold equal to first time-varying function after delivery of a second chamber pace during a first cardiac cycle and sets the first channel sensing threshold equal to second time-varying function after delivery of a second chamber pace during a subsequent cardiac cycle.

21. The device of claim 16 wherein the circuitry for rendering the first sensing channel refractory for a post-pace cross-chamber refractory period decreases the first channel sensing threshold from the post-pace cross-chamber maximum refractory value to the first steady-state value at the end of the post-pace cross-chamber refractory period.

22. The device of claim 16 wherein the circuitry for rendering the first sensing channel refractory for a post-pace cross-chamber refractory period decreases the first channel sensing threshold from the post-pace cross-chamber maximum refractory value to the first steady-state value at a decay rate derived from the measured peak amplitude of the post-pace far-field signal.

23. The device of claim 16 wherein the circuitry for rendering the first sensing channel refractory for a post-pace cross-chamber refractory period starts to decrease the first channel sensing threshold from the post-pace cross-chamber maximum refractory value to the first steady-state value after a delay interval derived from the measured peak amplitude of the post-pace far-field signal.

24. The device of claim 16 wherein the circuitry for measuring the peak amplitude of the post-pace far-field signal measures the peak amplitude by computing a statistical function of the measured peak amplitudes of the post-pace far-field signal generated in the first sensing channel after a second chamber pace during a specified number of cardiac cycles.

25. The device of claim 16 wherein the post-pace cross-chamber maximum refractory value is approximately 125% of the measured peak amplitude of the post-pace far-field signal.

26. The device of claim 16 further comprising:
   circuitry for rendering the first sensing channel refractory for a same-chamber refractory period upon detection of a first chamber sense or delivery of a first chamber pace by raising the first channel sensing threshold above the first channel steady-state value during the same-chamber refractory period; and,
   wherein the circuitry for rendering the first sensing channel refractory for a post-pace cross-chamber refractory period raises the first channel sensing threshold to a value dictated by either the post-pace cross-chamber refractory period or the same-chamber refractory period, whichever is greater, when the post-pace cross-chamber refractory period and the same-chamber refractory period overlap.

27. The device of claim 16 wherein the circuitry for rendering the first sensing channel refractory for post-pace cross-chamber refractory period raises the first sensing channel sensing threshold to an alternative maximum value during that period if the peak amplitude of the post-pace far-field signal has not yet been measured.

28. The device of claim 16 wherein the circuitry for measuring a peak amplitude of a post-pace far-field signal generated in the first sensing channel after a second chamber pace is delivered is configured to measure the peak amplitude only when a normal sinus rhythm is detected.

29. The device of claim 16 wherein the circuitry for measuring a peak amplitude of a post-pace far-field signal generated in the first sensing channel after a second chamber pace is delivered is configured to measure the peak amplitude by computing a statistical function of the measured peak amplitudes of the post-pace far-field signal during a training period consisting of a specified number of cardiac cycles, and further wherein the circuitry for rendering the first sensing channel refractory does not derive the post-pace cross-chamber maximum refractory value from the measured peak amplitude until after completion of the training period.

30. A method for operating a cardiac rhythm management device, comprising:
   sensing electrical activity in a first heart chamber through a first sensing channel and generating a first chamber sense when the sensed electrical activity exceeds a first channel sensing threshold which has a minimum level equal to a specified first channel steady-state value;
   sensing electrical activity in a second heart chamber through a second sensing channel and generating a second chamber sense when the sensed electrical activity exceeds a second channel sensing threshold which has a minimum level equal to a specified second channel steady-state value;
   measuring a peak amplitude of a post-event far-field signal generated in the first sensing channel after a specified second chamber event occurs; and,
   rendering the first sensing channel refractory for a cross-chamber post-event refractory period after occurrence of the second chamber event by raising the first channel sensing threshold above the first channel steady-state value, wherein the first channel sensing threshold is raised during the cross-chamber post-event refractory period to a maximum cross-chamber post-event refractory value derived from the measured peak amplitude of the post-event far-field signal.

31. The method of claim 30 wherein the specified second chamber event is a second chamber sense.

32. The method of claim 31 wherein the specified second chamber event is a second chamber pace.

33. The method of claim 30 wherein either of the first and second heart chambers may be a ventricle or an atrium.

34. The method of claim 30 wherein the first and second heart chambers are a ventricle and the contralateral ventricle.

35. The method of claim 30 wherein the peak amplitude of a post-event far-field signal generated in the first sensing channel after occurrence of a second chamber event is measured only when a normal sinus rhythm is detected.

36. The method of claim 30 wherein the peak amplitude of a post-event far-field signal generated in the first sensing channel after occurrence of a second chamber event is measured by computing a statistical function of the measured peak amplitudes of the post-event far-field signal during a training period consisting of a specified number of cardiac cycles, and further wherein the post-event cross-chamber maximum refractory value is not derived from the measured peak amplitude until after completion of the training period.

* * * * *

UNITED STATES PATENT AND TRADEMARK OFFICE
CERTIFICATE OF CORRECTION

| | |
|---|---|
| PATENT NO. | : 6,928,323 B2 |
| DATED | : August 9, 2005 |
| INVENTOR(S) | : Kim et al. |

It is certified that error appears in the above-identified patent and that said Letters Patent is hereby corrected as shown below:

Column 13,
Line 65, delete "a -first" and insert -- a first --.

Signed and Sealed this

Third Day of January, 2006

JON W. DUDAS
*Director of the United States Patent and Trademark Office*